United States Patent
Pan et al.

(10) Patent No.: US 8,974,389 B2
(45) Date of Patent: Mar. 10, 2015

(54) SYSTEM AND METHOD FOR DETECTING IRREGULAR BONE DEFECTS DURING DENTAL IMPLANT OSSEOINTEGRATION PROCESS

(75) Inventors: Min-Chun Pan, Pingzhen (TW); Jian-Zhi Chen, Taoyuan (TW)

(73) Assignee: National Central University, Jhongli (TW)

( * ) Notice: Subject to any disclaimer, the term of this patent is extended or adjusted under 35 U.S.C. 154(b) by 324 days.

(21) Appl. No.: 13/354,093

(22) Filed: Jan. 19, 2012

(65) Prior Publication Data

US 2013/0122458 A1 May 16, 2013

(30) Foreign Application Priority Data

Nov. 15, 2011 (TW) .............................. 100141666 A

(51) Int. Cl.
A61B 8/08 (2006.01)
A61C 19/04 (2006.01)
A61B 5/00 (2006.01)
A61C 8/00 (2006.01)

(52) U.S. Cl.
CPC ................ *A61B 8/0875* (2013.01); *A61C 19/04* (2013.01); *A61B 5/4542* (2013.01); *A61C 8/005* (2013.01)
USPC ............................ 600/437; 433/119; 433/215

(58) Field of Classification Search
CPC ........ A61B 8/0875; A61B 8/08; A61B 5/682; A61B 5/4542; A61C 19/04; A61C 8/005
See application file for complete search history.

(56) References Cited

U.S. PATENT DOCUMENTS

| | | | | |
|---|---|---|---|---|
| 6,890,302 B2* | 5/2005 | Oravecz et al. | ............... | 600/443 |
| 7,285,091 B2* | 10/2007 | Blodgett et al. | .............. | 600/437 |
| 2009/0306506 A1* | 12/2009 | Heger et al. | .................. | 600/443 |
| 2010/0228126 A1* | 9/2010 | Emery et al. | .................. | 600/439 |

OTHER PUBLICATIONS

Shung "Diagnostic Ultrasound Imaging and Blood Flow Measurements". Taylor & Francis Group. 2006.*

* cited by examiner

*Primary Examiner* — Long V Le
*Assistant Examiner* — Colin T Sakamoto
(74) *Attorney, Agent, or Firm* — Wang Law Firm, Inc.; Li K. Wang; Stephen Hsu

(57) ABSTRACT

A system and a method for detecting irregular bone defects during dental implant osseointegration process. The system comprises a detecting abutment, an ultrasonic driver, a signal receiving and analyzing device. When dental detection is performed, the detecting abutment is disposed on a substrate holder of a dental implant. The ultrasonic driver configures the piezoelectric transducers disposed on the detecting abutment to produce ultrasonic wave and transmits the ultrasonic wave to the contact surface between the dental implant and the alveolus bone. The piezoelectric transducers can receive the reflected wave caused by the each portion of the contact surface reflecting the ultrasonic wave and transform the reflected wave into time domain voltage signal. The signal receiving and analyzing device receives the time domain voltage signal to determine the depth, the severity and the location of the irregular bone defects of the contact surface.

9 Claims, 7 Drawing Sheets

SYSTEM AND METHOD FOR DETECTING IRREGULAR BONE DEFECTS DURING DENTAL IMPLANT OSSEOINTEGRATION PROCESS

CROSS-REFERENCE TO RELATED APPLICATION

This application claims the benefit of priority to Taiwan Patent Application No. 100141666, filed on Nov. 15, 2011, in the Taiwan Intellectual Property Office, the disclosure of which is incorporated herein in its entirety by reference.

BACKGROUND OF THE INVENTION

1. Field of the Invention

The present invention generally relates to a medical diagnostic technology, in particular to a system capable of precisely detecting irregular bone defects of the interface between the dental implant and the alveolus bone.

2. Description of the Related Art

With advances in medical technology, implant dentistry has become common for everyone. Implant dentistry is to place the dental implant made of metal into the jaw bone to replace the tooth root. The dental implant will be integrated into the jaw bone gradually during the period of osseointegration. Finally, the tooth crown is placed on the tooth. Thus, various detecting apparatuses are developed so as to effectively determine osseointegration between the jaw bone and the dental implant during the period of osseointegration.

Currently, there are many available apparatus for detecting osseointegration between the jaw bone and the dental implant. For example, one of the available apparatuses is to vibrate the dental implant by the ultrasonic wave and detect the vibration of the dental implant to receive the vibrating signal for determining osseointegration between the jaw bone and the dental implant, which would do some damage on the jaw bone and the dental implant during the period of osseointegration.

Another available detecting method is to vibrate a dental probe having an accelerometer on the tip thereof by a magnetic vibrating device and receive the vibrating signal from the dental implant by the accelerometer, which would also do some damage on the jaw bone and the dental implant during the period of osseointegration. Besides, the apparatus for the aforementioned method is complicated and expensive. Other invasive detecting methods have the same problems, too.

Another available detecting method is to cover the biomedical sensing materials over the surface of the dental implant and monitor the dental implant by a wireless detector. Meanwhile, the electromagnetic wave is emitted to the dental implant to produce the electronic signal and the magnetic signal by electromechanical energy conversion of the biomedical sensing materials in order to determine the stability of the dental implant. However, the aforementioned method is only used for determining the stability of the dental implant and cannot detect the locations, the severity and the depth of the irregular bone defects of the interface between the jaw bone and the dental implant.

The clinical X-ray apparatus is commonly applied to examine osseointegration between the jaw bone and the dental implant. However, the X-ray can just show 2-dimension image, which has a limit on helping doctors to diagnose osseointegration between the jaw bone and the dental implant. Accordingly, it is the primary object of the present invention to provide a non-invasive detecting system which is simple formation, can not cause damages on jaw bone and dental implant during the period of osseointegration and exactly detect the locations, the severity and the depth of the irregular bone defects of the interface between the jaw bone and the dental implant.

SUMMARY OF THE INVENTION

Therefore, it is a primary objective of the present invention to provide a system and a method for detecting irregular bone defects during dental implant osseointegration process to resolve the problems that the prior-art detecting system is apt to damage the jaw bone and the dental implant, of complex formation, expensive and fails to precisely determine the locations, the severity and the depth of the irregular bone defects of the interface between the jaw bone and the dental implant.

To achieve the foregoing objective, the present invention provides a system for detecting irregular bone defects during dental implant osseointegration process. The system comprises a detecting abutment, an ultrasonic driver, a signal receiving, and analyzing device. The detecting abutment comprises a main body and a plurality of piezoelectric transducers. The piezoelectric transducers are disposed around the main body and placed at regular intervals. The ultrasonic driver is used for driving the plurality of piezoelectric transducers to generate ultrasonic wave. The signal receiving and analyzing device is used for analyzing a time domain voltage signal transmitted from the plurality of piezoelectric transducers. Wherein, when dental detection is performed, the detecting abutment is disposed on a substrate holder of a dental implant. Next, the ultrasonic driver drives the plurality of piezoelectric transducers to generate the ultrasonic wave and transmits the ultrasonic wave to a an interface between the dental implant and an alveolus bone. The plurality of piezoelectric transducers receives reflected wave of the ultrasonic wave reflected by each portion of the interface and transforms the reflected wave into the time domain voltage signal. Finally, the signal receiving and analyzing device receives the time domain voltage signal to determine depth, severity and locations of the irregular bone defects of each portion of the interface between the dental implant and the alveolus bone.

To achieve the foregoing objective, the present invention further provides a method for detecting irregular bone defects during dental implant osseointegration process. The method comprises the following steps of: (1) fixing a detecting abutment on a substrate holder of a dental implant, the detecting abutment comprising a main body and a plurality of piezoelectric transducers; (2) driving the plurality of piezoelectric transducers disposed on the detecting abutment to generate ultrasonic wave by an ultrasonic driver and transmitting the ultrasonic wave to a an interface between the dental implant and an alveolus bone; (3) receiving reflected wave of the ultrasonic wave reflected by each portion of the interface between the dental implant and the alveolus bone and transforming the reflected wave into the time domain voltage signal by the plurality of piezoelectric transducers; and (4) receiving the time domain voltage signal by a signal receiving and analyzing device to determine depth, severity and locations of the irregular bone defects of each portion of the interface between the dental implant and the alveolus bone.

Preferably, the included angle between the central axis of each piezoelectric transducer and the central axis of the main body may be adjusted to reduce decay and error taking place during the transmission of the ultrasonic wave.

In an embodiment, the signal receiving and analyzing device may transform the time domain voltage signal into a frequency domain signal so as to perform analysis.

In an embodiment, the ultrasonic wave may be longitudinal wave or transverse wave.

Preferably, the piezoelectric transducer may be a piezoelectric ceramic plate.

The system and the method for detecting the irregular bone defects during the dental implant osseointegtation process according to the present invention have one or more the following advantages:

(1) The system for detecting the irregular bone defects during the dental implant osseointegtation process is simple formation, low-cost, which can effective reduce the cost of the dental implant surgery.

(2) The system for detecting the irregular bone defects during the dental implant osseointegtation process uses the detecting abutment to act as both ultrasonic transmitter and receiver, which will not cause damages on the jaw bone and the dental implant during the period of osseointegation.

(3) The system for detecting the irregular bone defects during the dental implant osseointegation process uses a plurality of piezoelectric transducers to receive the reflected wave and transform the reflected wave into the time domain voltage signal. The time domain voltage signal is transmitted to the signal receiving and analyzing device to immediately perform comparison and analysis. Accordingly, the system according to the present invention can exactly detect the locations, the severity and the depth of the irregular bone defects of the interface between the jaw bone and the dental implant.

BRIEF DESCRIPTION OF THE DRAWINGS

The detailed structure, operating principle and effects of the present invention will now be described in more details hereinafter with reference to the accompanying drawings that show various embodiments of the invention as follows.

DETAILED DESCRIPTION OF THE PREFERRED EMBODIMENTS

The technical content of the present invention will become clear by the detailed description of the following embodiments and the illustration of related drawings as follows.

Figure 1:
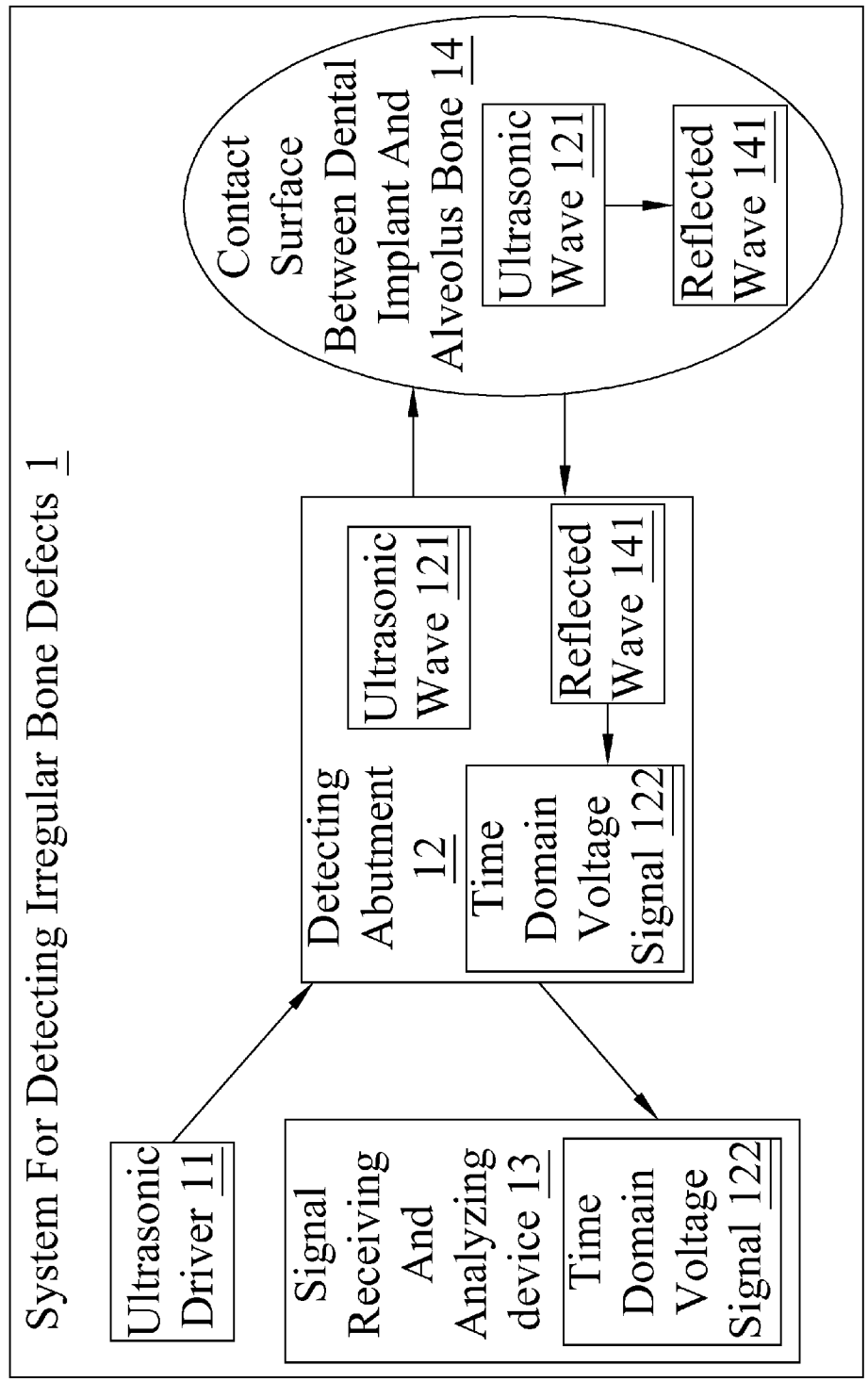
FIG. 1 is a block diagram of the system for detecting the irregular bone defects in accordance with the present invention.

With reference to FIG. 1 for a block diagram of the system for detecting the irregular bone defects in accordance with the present invention. As shown in FIG. 1, the system for detecting the irregular bone defects 1 comprises an ultrasonic driver 11, a detecting abutment 12 and a signal receiving and analyzing device 13. The detecting abutment 12 comprises a main body and a plurality of piezoelectric transducers. The piezoelectric transducers are disposed around the main body and placed at regular intervals. The material of the main body is the same as which of the dental implant. Generally speaking, the main body is made of metal, such as Ti, etc. Pure Ti is commonly applied to medical purposes, such like dental implant surgery due to its excellent human tissue compatibility.

The included angle between the central axis of each piezoelectric transducer and the central axis of the main body can be adjusted according to actual requirements to significantly reduce the decay and the error taking place while the ultrasonic wave is transmitted, which can exactly enhance the precision of the system for detecting irregular bone defects 1. The piezoelectric transducer can be made of any piezoelectric material, such as piezoelectric ceramic plate.

The ultrasonic driver 11 can drive the plurality of piezoelectric transducers to vibrate at high speed in order to generate the ultrasonic wave 121 and then transmit the ultrasonic wave 121 to the interface between the dental implant and the alveolus bone 14. The decay of the acoustic wave between the main body and the dental implant will not take place during the transmission of the ultrasonic wave 121 if the material of the main body is the same as which of the dental implant, and there is no gap between the main body and the dental implant. Wherein, the ultrasonic wave 121 may be longitudinal wave or transverse wave.

The plurality of piezoelectric transducers can receive the reflected wave 141 that each portion of the interface between the dental implant and the alveolus bone 14 reflects the ultrasonic wave 121. The plurality of piezoelectric transducers can transform the reflected wave 141 into the time domain voltage signal 122 and transmit the time domain voltage signal 122 to the signal receiving and analyzing device 13 because the piezoelectric effect is reversible. In addition, the user can adjust the piezoelectric transducers to transmit or receive signal simultaneously or in turn according to actual requirements.

Since the irregular bone defects of the interface between the dental implant and the alveolus bone 14 will cause different acoustic impedance, the signal receiving and analyzing device 13 can precisely detect the depth and the locations of the irregular bone defects of each portion of the interface between the dental implant and the alveolus bone 14 by analyzing the received time domain voltage signal 122. Besides, the signal receiving and analyzing device 13 can also detect the size of the irregular bone defects by analyzing the amplitude of the received time domain voltage signal 122 in order to determine the severity of the irregular bone defects. When the irregular bone defect is slight, the time domain voltage signal 122 received by the signal receiving and analyzing device 13 will have high amplitude because the transmitted signal passed through small gaps or slight defects. On the contrary, when the irregular bone defect is severe, the time domain voltage signal 122 received by the signal receiving and analyzing device 13 will have low amplitude because the transmitted signal passed through large gaps or severe defects. Accordingly, the signal receiving and analyzing device 13 can precisely detect the severity of the irregular bone defects of the interface between the dental implant and the alveolus bone 14 by analyzing the amplitude of the received time domain voltage signal 122. In addition, the signal receiving and analyzing device 13 can further transform the time domain voltage signal 122 into a frequency domain signal to perform further analysis.

More specifically, the plurality of piezoelectric transducers can receive the reflected wave 141 that each portion of the interface between the dental implant and the alveolus bone 14 reflects the ultrasonic wave 121 and transform the reflected wave 141 into the time domain voltage signal 121. Then the signal receiving and analyzing device receives the time domain voltage signal 121 to immediately perform analysis and comparison. Thus, the system according to the present invention can provide higher precision in determining the depth, the severity and the locations of the irregular bone defects of each portion of the interface between the dental implant and the alveolus bone 14 as compared with prior-art detecting systems.

Figure 2:
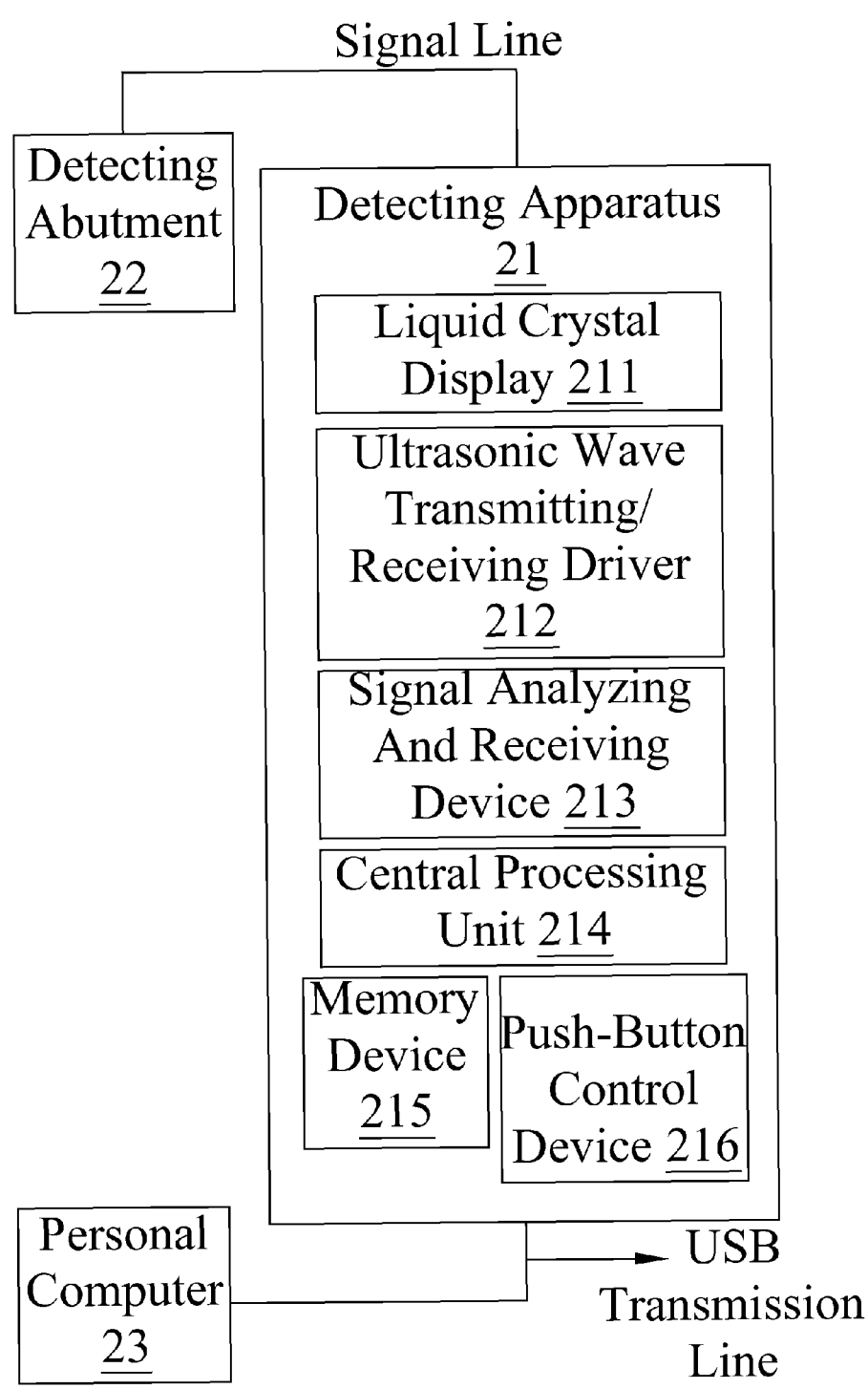
FIG. 2 is a block diagram of the second preferred embodiment of the system for detecting the irregular bone defects in accordance with the present invention.

With reference to FIG. 2 for a block diagram of the second preferred embodiment of the system for detecting the irregular bone defects in accordance with the present invention. As shown in FIG. 2, the system for detecting the irregular bone defects 2 comprises the detecting apparatus 21, the detecting abutment 22 and the personal computer 23. Wherein, the detecting apparatus 21 comprises the liquid crystal display 211, the ultrasonic wave transmitting/receiving driver 212, the signal analyzing and receiving device 213, the central processing unit 214, the memory device 215 and the push-button control device 216. The detecting abutment 22 may be connected to the detecting apparatus 21 by various ways. In the embodiment, the detecting abutment 22 is connected to the detecting apparatus 21 via a signal line.

The user can operate the detecting apparatus 21 through the push-button control device 216. The central processing unit 214 can control the ultrasonic wave transmitting/receiving driver 212 to drive the detecting abutment 22 in order to generate ultrasonic wave according to the instruction input by the user and then transmit the ultrasonic wave to the interface of the implant and the alveolus bone. Similarly, the plurality of piezoelectric transducers disposed on the detecting abutment 22 can receive the reflected wave of the ultrasonic wave reflected by each portion of the interface between the dental implant and the alveolus bone. Next, the reflected wave will be transformed into time domain voltage signal by the plurality of piezoelectric transducers and then the time domain voltage signal will be transmitted to the detecting apparatus 21.

The central processing unit 214 can transmit the time domain voltage signal to the signal analyzing and receiving device 213 to perform analysis and display which on the liquid crystal display 211. Accordingly, osseointegration between the implant and the alveolus bone can be effectively determined. The central processing unit 214 can further save all detecting information in the memory device 215. Similarly, the signal analyzing and receiving device 213 can further transform the time domain voltage signal into a frequency domain signal to perform further analysis.

The personal computer 23 is connected to the detecting apparatus 21 via the USB transmission line. Moreover, the personal computer 231 can further download the detecting information saved in the memory device 215. The user not only can use the personal computer 231 to effectively manage the data of each patient through management software, but also can directly control the operation of the detecting apparatus 21 via the personal computer 23.

Figure 3:
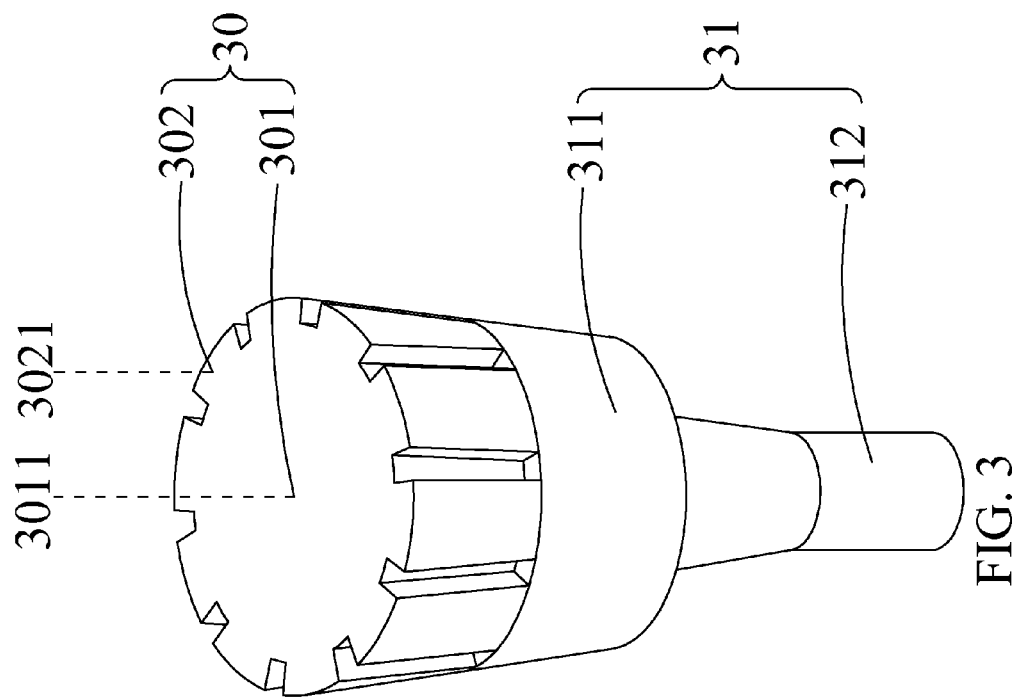
FIG. 3 is a schematic view of the detecting abutment of the third preferred embodiment of the system for detecting the irregular bone defects in accordance with the present invention.

With reference to FIG. 3 for a schematic view of the detecting abutment of the third preferred embodiment of the system for detecting the irregular bone defects in accordance with the present invention. As shown in FIG. 3, the detecting abutment 30 comprises the main body 301 and the plurality of rectangular piezoelectric transducers 302. Under normal circumstances, the intervals between the piezoelectric transducers 302 should be as small as possible to obtain precisely detecting result. When dental detection is performed, the detecting abutment 30 is disposed on the substrate holder 311 of the dental implant 31 and the implant 312 is embedded into the alveolus bone. The central axis 3021 of each rectangular piezoelectric transducer 302 and the central axis 3011 of the main body 301 can be adjusted according to actual requirements so as to minimize the decay and the error taking place during the transmission of the ultrasonic wave.

Figure 4:
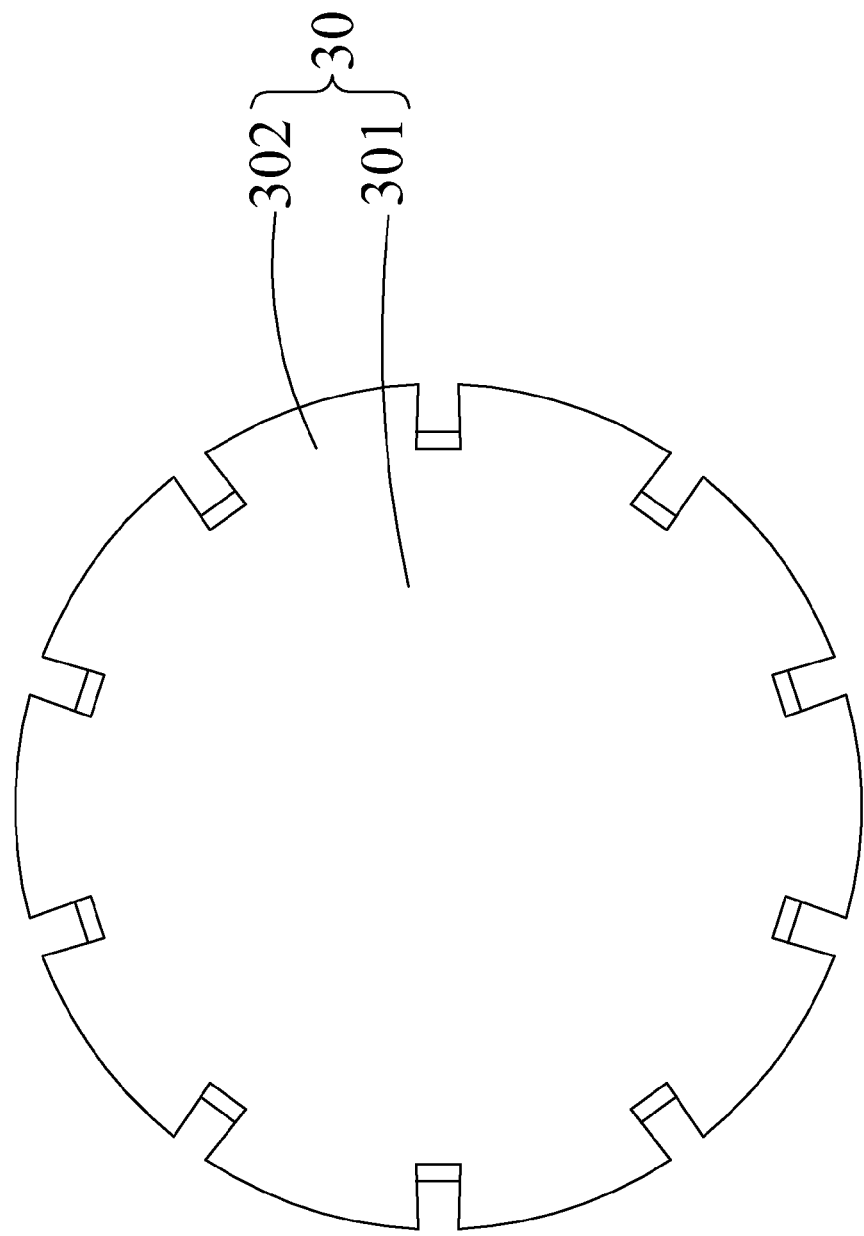
FIG. 4 is a top view of the detecting abutment of the third preferred embodiment of the system for detecting the irregular bone defects in accordance with the present invention.

With reference to FIG. 4 for a top view of the detecting abutment of the third preferred embodiment of the system for detecting the irregular bone defects in accordance with the present invention. As shown in FIG. 4, the detecting abutment 30 has ten rectangular piezoelectric plates 302 disposed around the main body 301 and having the same size. The piezoelectric plates 302 are placed at regular intervals. The arrangement of the embodiment is just for example; the shape and the size of the piezoelectric plate 302 and the main body 301 can be adjusted according to actual requirements; the present invention is not limited to such arrangement only.

Figure 5:
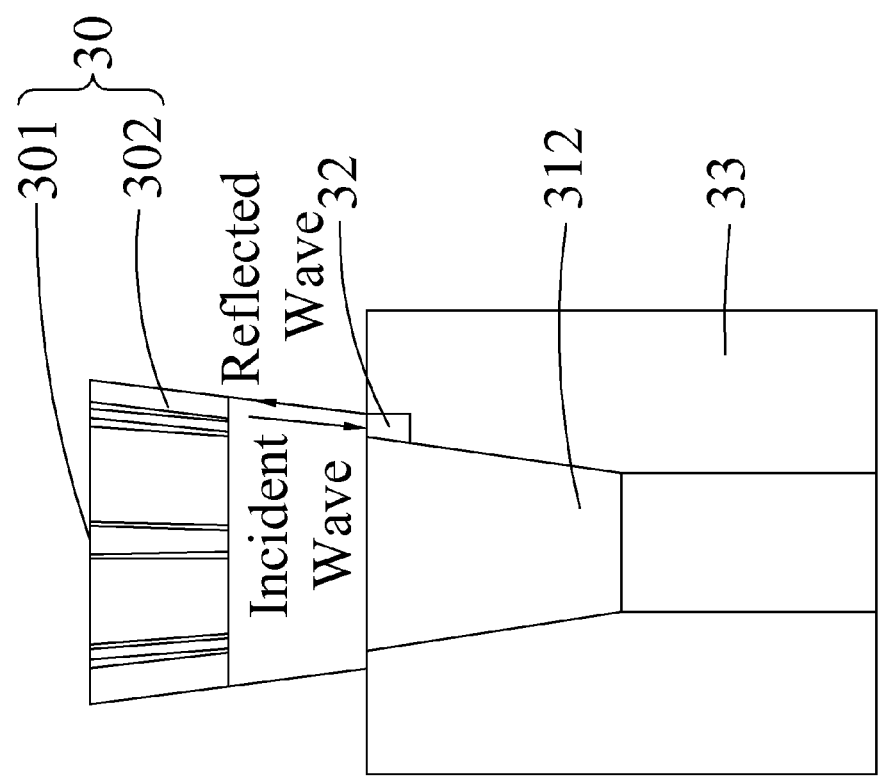
FIG. 5 is a schematic view of the actual implement of the third preferred embodiment of the system for detecting the irregular bone defects in accordance with the present invention.

With reference to FIG. 5 for a schematic view of an actual implement of the third preferred embodiment of the system for detecting the irregular bone defects in accordance with the present invention. As shown in FIG. 5, when osseointegration detection is performed, the detecting abutment 30 is disposed on the substrate holder 311 of the dental implant 31 and the plurality of piezoelectric plates 302 is drived to generate ultrasonic wave. As shown in FIG. 5, the incident wave emitted from the piezoelectric plates 302 are transmitted to the irregular bone defect 32. When the acoustic pressure of the incident wave is in contact with the air, the ultrasonic wave will reflect an acoustic pressure due to different acoustic impendence. The acoustic pressure will be received by the piezoelectric plates 302 and transformed into a time domain voltage signal. Since ten piezoelectric plates 302 are placed at different places, the depth and the locations of the irregular bone defects of the interface between the implant 312 and the alveolus bone 33 can be determined by performing comparison and analysis on the time domain voltage signal transmitted from each piezoelectric plant 302. Besides, the size of the irregular bone defects between the implant 312 and the alveolus bone 33 can be precisely determined by analyzing the amplitude of the received time domain voltage signal. The arrangement of the embodiment is just for example; the number, the shape and the size of the piezoelectric plate 302 can be adjusted according to actual requirements; the present invention is not limited to such arrangement only.

Figure 6:
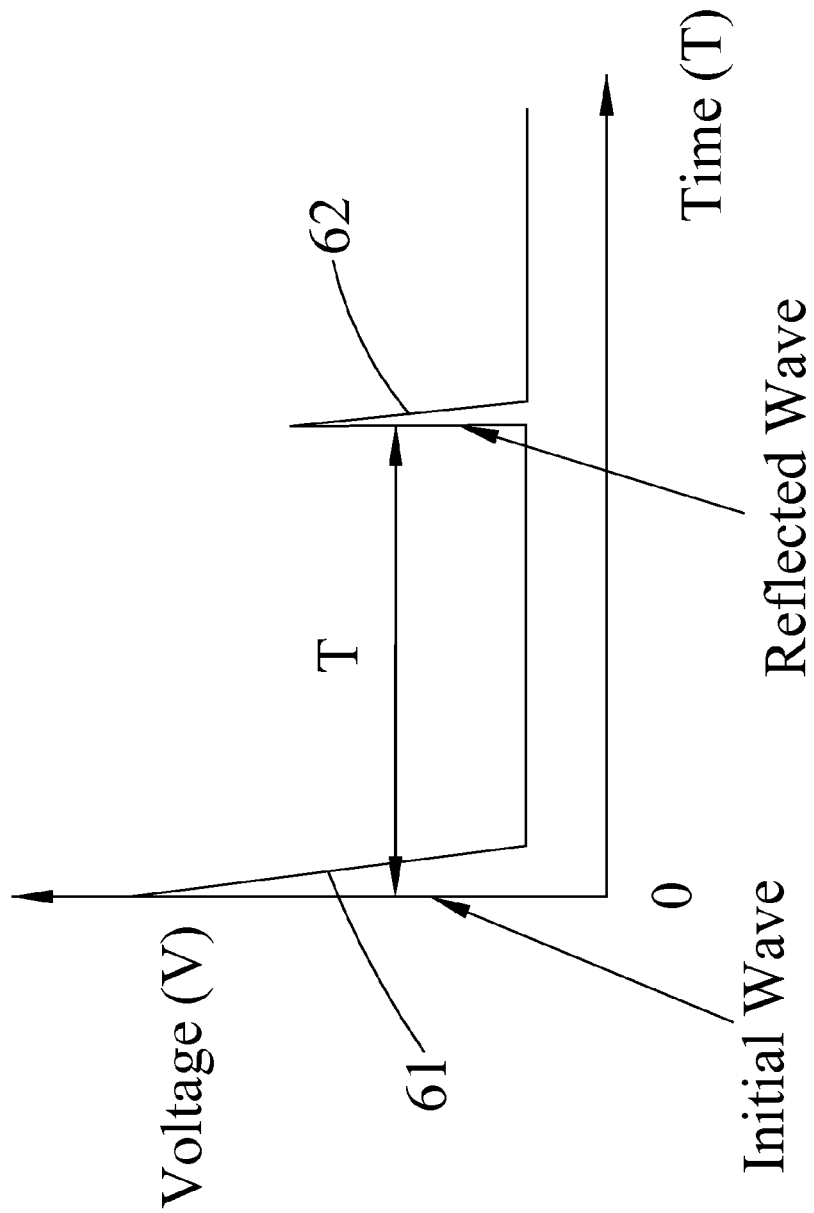
FIG. 6 is a voltage signal analyzing diagram of the third preferred embodiment of the system for detecting the irregular bone defects in accordance with the present invention.

Please refer to FIGS. 5 and 6. FIG. 6 is a voltage signal analyzing diagram of the third preferred embodiment of the system for detecting the irregular bone defects in accordance with the present invention. As shown in FIGS. 5 and 6, when the incident wave emitted from the piezoelectric plants 302 is transmitted to the irregular bone defect 32, the reflected wave 62 as shown in FIG. 6 will be produced because the irregular bone defect 32 has different acoustic impendence. The time interval of the initial wave and the reflected wave is T. Accordingly, a correlation can be obtained as follows:

$$T=(2\times L)/V \tag{1}$$

Wherein, T is the time interval of the initial wave and the reflected wave; V is the wave velocity, which may be longitudinal wave or transverse wave; L is the depth of the irregular bone defect. In this way, the system for detecting irregular bone defects according to the present invention can precisely detecting the depth of the bone defect of the interface between the implant 312 and the alveolus bone 33.

Even though the concept of the method for detecting irregular bone defects during dental implant osseointegration process of the present invention has been described in the aforementioned process of the system for detecting the irregular bone defects during dental implant osseointegration process in accordance with the present invention, yet a flow chart is provided for further illustrating the present invention as follows.

Figure 7:
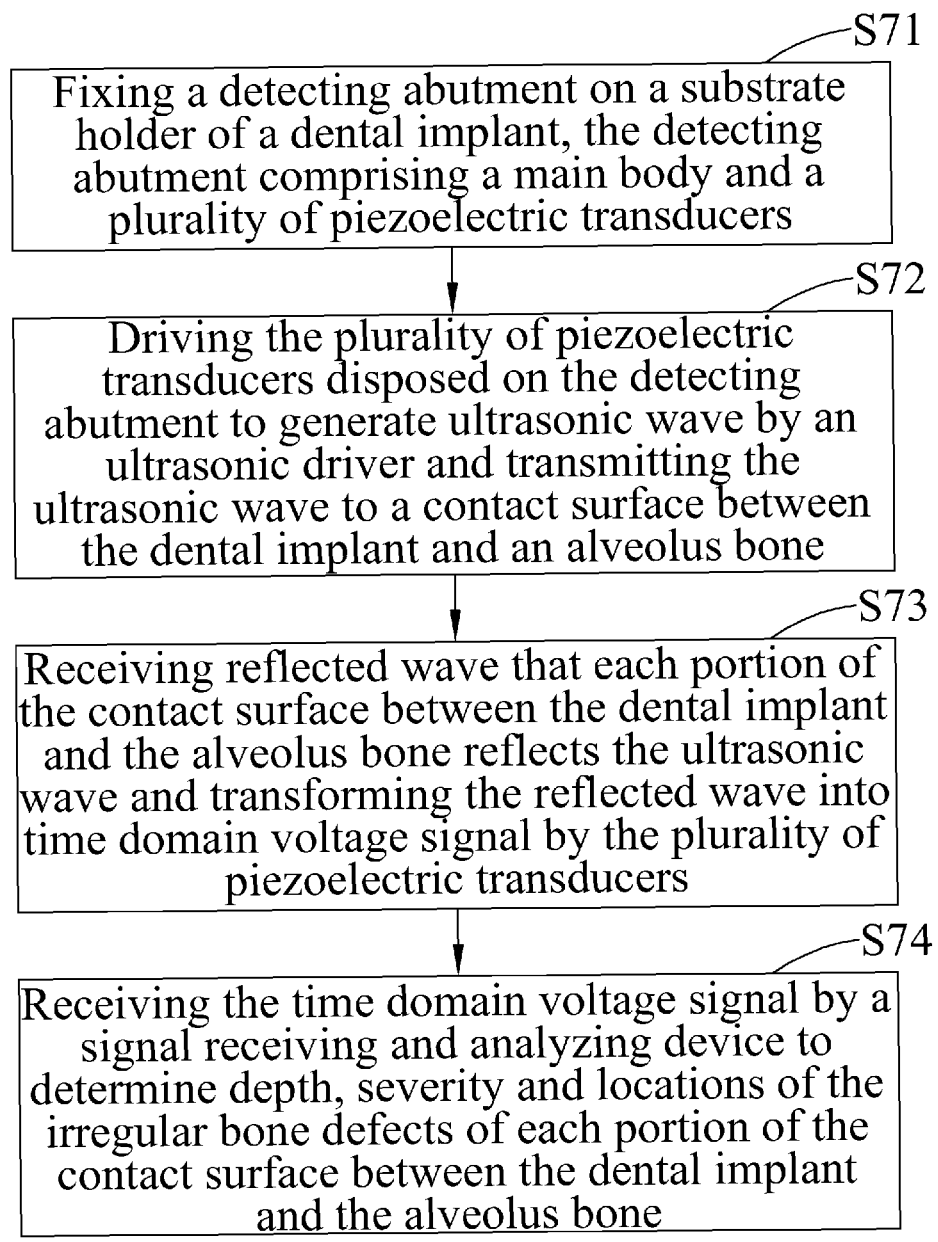
FIG. 7 for a flow chart of the method for detecting irregular bone defects during dental implant osseointegration process in accordance with the present invention.

With reference to FIG. 7 for a flow chart of the method for detecting irregular bone defects during dental implant osseointegration process in accordance with the present invention. The method comprises the following steps of:

S71: fixing a detecting abutment on a substrate holder of a dental implant, the detecting abutment comprising a main body and a plurality of piezoelectric transducers.

S72: driving the plurality of piezoelectric transducers disposed on the detecting abutment to generate ultrasonic wave by an ultrasonic driver and transmitting the ultrasonic wave to a an interface between the dental implant and an alveolus bone.

S73: receiving reflected wave that each portion of the interface between the dental implant and the alveolus bone reflects the ultrasonic wave and transforming the reflected wave into the time domain voltage signal by the plurality of piezoelectric transducers.

S74: receiving the time domain voltage signal by a signal receiving and analyzing device to determine depth, severity and locations of the irregular bone defects of each portion of the interface between the dental implant and the alveolus bone.

The detailed description and implementation method of the method for detecting irregular bone defects during dental implant osseointegration process in accordance with the present invention have been described in the section of the system for detecting the irregular bone defects during dental implant osseointegration process already, and thus will not be repeated.

In summation of the description above, the system according to the present invention is simple formation, low-cost, which can effectively reduce the cost of the dental implant surgery. In addition, the system according to the present invention uses the detecting abutment to act as both ultrasonic transmitter and receiver, which will not cause damages on the jaw bone and the dental implant during the period of osseointegration. Moreover, the system according to the present invention uses a plurality of piezoelectric transducers to receive reflected wave and transform the reflected wave into a time domain voltage signal. The time domain voltage signal is transmitted to a signal receiving and analyzing device to immediately perform comparison and analysis. The time domain voltage signal is transmitted to a signal receiving and analyzing device to immediately perform comparison and analysis. Accordingly, the system according to the present invention can exactly detect the locations, the severity and the depth of the irregular bone defects of the interface between the jaw bone and the dental implant. Accordingly, the present invention has advantages and overcomes the shortcomings of the prior art.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A system for detecting irregular bone defects during dental implant osseointegration process, comprising:
    a dental implant, comprising a substrate holder and an implant, wherein the implant of the dental implant is configured to be embedded into an alveolus bone, and wherein the dental implant is made of metal;
    a detecting abutment, disposed on the substrate holder of the dental implant, and the detecting abutment comprising a main body and a plurality of piezoelectric transducers, the plurality of piezoelectric transducers being disposed around a periphery of the main body and placed at regular intervals;
    an ultrasonic driver, for driving the plurality of piezoelectric transducers to generate ultrasonic wave; and
    a signal receiving and analyzing device, for analyzing a time domain voltage signal transmitted from the plurality of piezoelectric transducers;
    wherein the ultrasonic driver is configured to drive the plurality of piezoelectric transducers to generate the ultrasonic wave and transmitting the ultrasonic wave to an interface between the dental implant and the alveolus bone,
    wherein the plurality of piezoelectric transducers are configured to receive a reflective wave reflected by each portion of the interface, and the reflective wave is further transformed into the time domain voltage signal,
    wherein the signal receiving and analyzing device is configured to receive the time domain voltage signal and to determine depth, severity and locations of the irregular bone defects of each portion of the interface between the dental implant and the alveolus bone, and
    wherein a material of the main body of the detecting abutment is the same as which of the dental implant.

2. The system for detecting irregular bone defects of the claim 1, wherein the signal receiving and analyzing device transforms the time domain voltage signal into a frequency domain signal so as to perform analysis.

3. The system for detecting irregular bone defects of the claim 1, wherein the ultrasonic wave is longitudinal wave or transverse wave.

4. The system for detecting irregular bone defects of the claim 1, wherein the piezoelectric transducers are piezoelectric ceramic plates.

5. A method for detecting irregular bone defects during dental implant osseointegration process, comprising the following steps of:
    embedding an implant of a dental implant into an alveolus bone, wherein the dental implant is made of metal;
    disposing a plurality of piezoelectric transducers around a periphery of a main body of a detecting abutment at regular intervals;
    fixing the detecting abutment on a substrate holder of the dental implant, wherein a material of the main body of the detecting abutment is the same as which of the dental implant;
    driving the plurality of piezoelectric transducers disposed on the detecting abutment to generate ultrasonic wave by an ultrasonic driver and transmitting the ultrasonic wave to an interface between the dental implant and the alveolus bone;
    receiving reflected wave of the ultrasonic wave reflected by each portion of the interface between the dental implant and the alveolus bone; and transforming the reflected wave into the time domain voltage signal by the plurality of piezoelectric transducers; and receiving the time domain voltage signal by a signal receiving and analyzing device to determine depth, severity and locations of the irregular bone defects of each portion of the interface between the dental implant and the alveolus bone.

6. The method for detecting irregular bone defects of the claim 5, further comprising the following step of:

adjusting an included angle between a central axis of each piezoelectric transducer and a central axis of the main body in order to reduce decay and error taking place during the transmission of the ultrasonic wave, wherein the central axis of the main body is perpendicular to an interface between the main body and the substrate holder of the dental implant, and the central axis of each piezoelectric transducer is perpendicular to a radial axis in the periphery of the main body.

7. The method for detecting irregular bone defects of the claim 6, further comprising the following step of:

transforming the time domain voltage signal into a frequency domain signal by the signal receiving and analyzing device.

8. The method for detecting irregular bone defects of the claim 6, wherein the ultrasonic wave is longitudinal wave or transverse wave.

9. The method for detecting irregular bone defects of the claim 6, wherein the piezoelectric transducers are piezoelectric ceramic plates.

* * * * *